United States Patent
Ahn et al.

(10) Patent No.: US 11,589,802 B2
(45) Date of Patent: Feb. 28, 2023

(54) REAL-TIME PARATHYROID IMAGING DEVICE

(71) Applicant: PUKYONG NATIONAL UNIVERSITY INDUSTRY-UNIVERSITY COOPERATION FOUNDATION, Busan (KR)

(72) Inventors: Yeh-Chan Ahn, Busan (KR); Sung-Won Kim, Busan (KR); Kang-Dae Lee, Busan (KR); Hyoung-Shin Lee, Busan (KR); Chul-Ho Oak, Busan (KR); Seo-Hyun Song, Busan (KR); Hyun-Wook Kang, Busan (KR); Joon-Shik You, Laguna Niguel, CA (US)

(73) Assignee: PUKYONG NATIONAL UNIVERSITY INDUSTRY-UNIVERSITY COOPERATION FOUNDATION, Busan (KR)

(*) Notice: Subject to any disclaimer, the term of this patent is extended or adjusted under 35 U.S.C. 154(b) by 846 days.

(21) Appl. No.: 16/338,394

(22) PCT Filed: Sep. 4, 2017

(86) PCT No.: PCT/KR2017/009650
§ 371 (c)(1),
(2) Date: Mar. 29, 2019

(87) PCT Pub. No.: WO2018/062709
PCT Pub. Date: Apr. 5, 2018

(65) Prior Publication Data
US 2020/0022640 A1    Jan. 23, 2020

(30) Foreign Application Priority Data
Sep. 30, 2016    (KR) .................... 10-2016-0126404

(51) Int. Cl.
*A61B 5/00* (2006.01)
*A61B 90/30* (2016.01)
*G02B 5/20* (2006.01)

(52) U.S. Cl.
CPC .......... *A61B 5/4227* (2013.01); *A61B 5/0071* (2013.01); *A61B 5/0077* (2013.01);
(Continued)

(58) Field of Classification Search
CPC ........................... A61B 5/4227; A61B 5/0077
See application file for complete search history.

(56) References Cited

U.S. PATENT DOCUMENTS

| | | | |
|---|---|---|---|
| 7,365,844 B2 | 4/2008 | Richards-Kortum et al. | |
| 2008/0228083 A1* | 9/2008 | Wu | A61B 5/0059 600/475 |
| 2022/0007997 A1* | 1/2022 | Mannoh | G01N 21/6456 |

FOREIGN PATENT DOCUMENTS

| | | |
|---|---|---|
| JP | 2004-525697 A | 8/2004 |
| JP | 2012-037472 A | 2/2012 |

(Continued)

OTHER PUBLICATIONS

Korean Patent Abstract (in English) of KR Patent App. Pub. No. 10-2010-0106965 A, Pub. Date Oct. 4, 2010, downloaded Mar. 29, 2019 from https://worldwide.espacenet.com/.

(Continued)

*Primary Examiner* — Joseph M Santos Rodriguez
(74) *Attorney, Agent, or Firm* — Barcelo, Harrison & Walker, LLP (57) ABSTRACT

The present invention relates to a real-time parathyroid imaging device, and a real-time parathyroid imaging device for displaying only a parathyroid in a thyroid with a separate mark, the real-time parathyroid imaging device including: a light source configured to emit light to a thyroid and excite (Continued)

a parathyroid; a detector configured to detect an emission spectrum of the parathyroid excited and emitted by the light source; an excitation filter disposed in front of the light source; and an emission filter disposed in front of the detector. When central Compartment Neck Dissection (CCND) for thyroidectomy is performed, the present invention clearly marks a parathyroid by an autofluorescent image, thereby allowing a surgeon to more simply and safely perform the CCND while leaving the parathyroid.

14 Claims, 9 Drawing Sheets

(52) U.S. Cl.
CPC .............. *A61B 90/30* (2016.02); *G02B 5/208* (2013.01); *A61B 2090/309* (2016.02)

(56) References Cited

FOREIGN PATENT DOCUMENTS

| | | |
|---|---|---|
| KR | 10-2010-0106965 A | 10/2010 |
| KR | 10-2014-0034124 A | 3/2014 |
| KR | 10-2015-0007679 A | 1/2015 |
| KR | 10-2016-0008196 A | 1/2016 |
| WO | WO-2009064911 A2 * | 5/2009 .............. A61B 3/10 |

OTHER PUBLICATIONS

Korean Patent Abstract (in English) of KR Patent App. Pub. No. 10-2015-0007679 A, Pub. Date Jan. 21, 2015, downloaded Mar. 29, 2019 from https://worldwide.espacenet.com/.

Korean Patent Abstract (in English) of KR Patent App. Pub. No. 10-2016-0008196 A, Pub. Date Jan. 21, 2016, downloaded Mar. 29, 2019 from https://worldwide.espacenet.com/.

Japanese Patent Abstract (in English) of JP Patent App. Pub. No. 2004525697 A, Pub. Date Aug. 26, 2004, downloaded Mar. 29, 2019 from https://worldwide.espacenet.com/.

Korean Patent Abstract (in English) of KR Patent App. Pub. No. 10-2014-0034124, Pub. Date Mar. 19, 2014, downloaded Mar. 29, 2019 from https://worldwide.espacenet.com/.

Japanese Patent Abstract (in English) of JP Patent App. Pub, No. 2012037472 A, Pub. Date Feb. 23, 2012, downloaded Mar. 29, 2019 from https://worldwide.espacenet.com/.

* cited by examiner

REAL-TIME PARATHYROID IMAGING DEVICE

CROSS-REFERENCE TO RELATED APPLICATIONS

This application is the national stage entry for International Patent Cooperation Treaty Application PCT/KR2017/009650, filed on 4 Sep. 2017, which claims priority from Korean Patent Application No. 10-2016-0126404, filed on 30 Sep. 2016, in the Korean Intellectual Property Office. The entire contents of said applications are incorporated herein by reference for all purposes.

BACKGROUND OF THE INVENTION

Technical Field

The present invention relates to a real-time parathyroid imaging device, and particularly, to a real-time parathyroid imaging device, which uses a light source, a detector, and a filter, and detects autofluorescence of a parathyroid emitted after being excited by the light source by using the detector, thereby allowing the dissection of a thyroid excluding the parathyroid when thyroidectomy is performed.

Background Art

According to a recent increasing tendency of thyroid cancer, thyroidectomy for removing tumor of the thyroid together with the thyroid has been frequently performed, but the thyroidectomy has particularly cautionary things. That is, in the thyroidectomy for removing tumor of the thyroid, it is very important to preserve parathyroid present near the thyroid.

Because the parathyroid is an important gland that maintains calcium homeostasis in our body, the parathyroid cannot be dissected and removed. However, the parathyroid is a very small and delicate organ having weight of 35 to 45 mg and a size of about 4×5×2 mm, so that it is not easy to visually distinguish the parathyroid from the thyroid and surrounding tissues, such as a lymphatic gland, with naked eyes.

Figure 1:
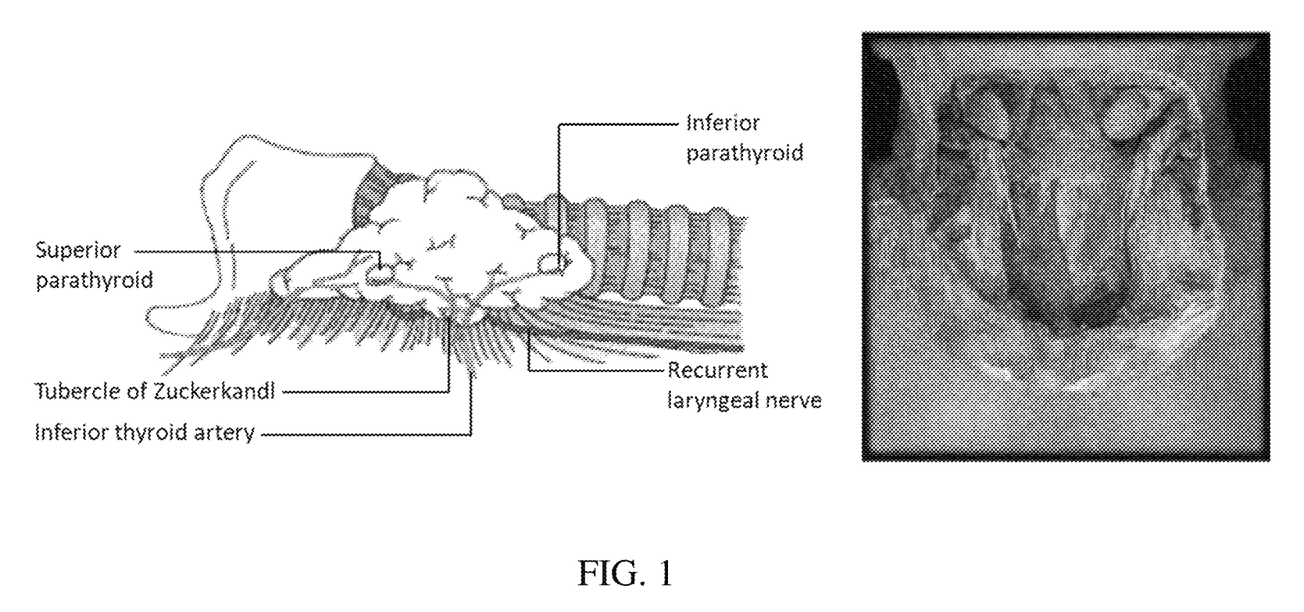
FIG. 1 is a diagram illustrating a location of a parathyroid, and a left diagram illustrates locations of the parathyroids on the upper and lower right portions and a right diagram illustrates a location of the parathyroid viewed on the front of a neck.

FIG. 1 illustrates a position of a parathyroid, and the parathyroid is located at the back of a thyroid located at the center of an anterior side of a neck. There are usually four parathyroids one each on the upper and lower left portions and one each on the upper and lower right portions.

Figure 2:
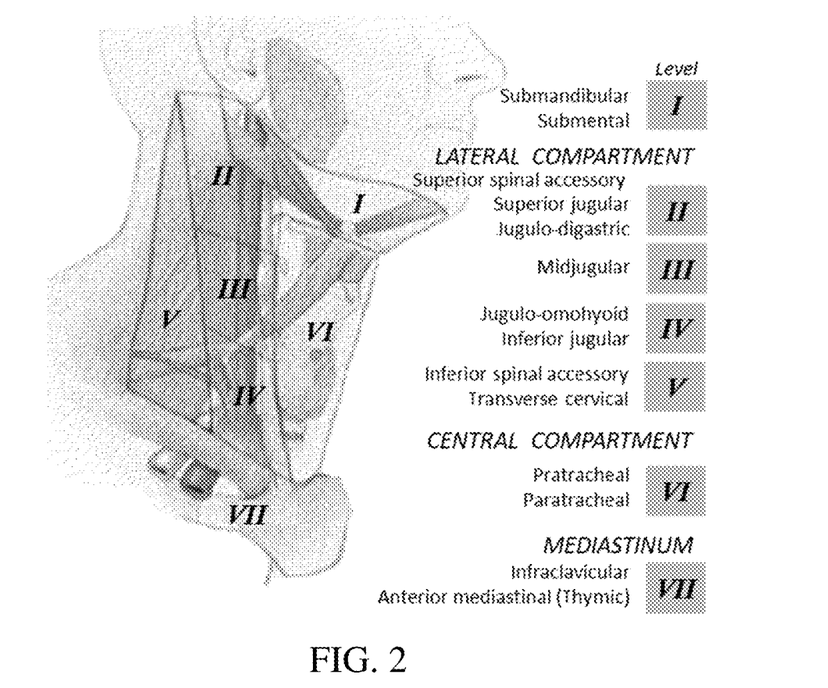
FIG. 2 is a diagram illustrating subgroups of a lymph node of a neck portion.

In the meantime, during the thyroidectomy for removal of the thyroid tumor, the peripheral lymph node (level 6) is dissected simultaneously considering the possibility of cancer metastasis. This is called a Central Compartment Neck Dissection (CCND). Further, as illustrated in FIG. 2, the division of the lymph node into subgroups according to a position is called a level system. The level system includes a total of seven divisions. However, the thyroid among the seven levels is included in a section of level 6, and thyroid papillary carcinoma is characterized by an easy metastasis to a lymph node of level 6. Due to the characteristic, when the CCND is performed, a normal lymph node is very small, so that it is almost impossible to visually check the normal lymph node. Accordingly, during lymphadenectomy, both the adipose tissue and the connective tissue containing the lymph node are removed together. Herein, it is important to recognize a position of a parathyroid. The reason for this is that it is not easy to distinguish the parathyroid from the surrounding adipose tissue and/or connective tissue unless a surgeon is a skilled surgeon in the section of level 6.

Accordingly, in order to safely perform the CCND while leaving the parathyroid, only a surgeon skilled in the CCND is restrictively involved in the procedure.

As a related prior art document, Korean Patent Application Laid-Open No. 10-2014-0034124, Japanese Patent Application Laid-Open No. 2012-037472, and the like may be referred.

DISCLOSURE

Technical Problem

The present invention is conceived to solve the foregoing problems, and an object of the present invention is to provide a real-time parathyroid imaging device, which detects autofluorescence of a parathyroid with a light source, a detector, and filters by using a feature that the parathyroid emits stronger autofluorescence than that of a thyroid and surrounding tissues, performs imaging on the detected autofluorescence in real time and displays the image on a screen, thereby providing convenience to an operator when thyroidectomy is performed.

Technical Solution

In order to achieve the foregoing object, a real-time parathyroid imaging device for displaying a parathyroid near a thyroid with a separate mark according to the present invention includes: a light source configured to emit light to a thyroid and excite a parathyroid; a detector configured to detect an emission spectrum of the parathyroid excited by the light source; an excitation filter disposed in front of the light source; and an emission filter disposed in front of the detector.

The light source may be a Light Emitting Diode (LED) or laser diode light source, and the LED or laser diode light source may be a collimated light source having a predetermined peak wavelength.

The detector may be a Digital Single Lens Reflex (DSLR) camera or various cameras mounted with a Charged Coupled Device (CCD), a Complementary Metal Oxide Semiconductor (CMOS), or a near-infrared sensor.

The excitation filter may be a band-pass filter having a predetermined peak wavelength and band width, the emission filter may be a band-pass filter having a predetermined peak wavelength and band width, and the excitation filter and the emission filter may be band-pass filters having different peak wavelengths and bandwidths.

The real-time parathyroid imaging device may further include an infrared ray illuminator which emits infrared rays toward the thyroid.

The mark marking the emission spectrum of the parathyroid by the light source detected by the detector may be an autofluorescent image.

The light source may be a laser diode light source, and the real-time parathyroid imaging device may further include a notch filter disposed in front of the detector so that all of the autofluorescence spectrums, except for a narrow-band light source spectrum by the laser diode light source, reaches the detector.

In order to provide an image in which a visible ray image and an autofluorescent image overlap, transmissivity of visible rays of the notch filter may be limited to be low and transmissivity of near-infrared rays may be adjusted to be relatively large so that the two images make an overlapped image with the best contrast.

In order to provide an image in which a visible ray image and an autofluorescent image overlap, the notch filter may include a low-pass filter and a high-pass filter each of which a filter region is independently adjusted so that the two images make an overlapped image with the best contrast.

An imaging device according to another aspect of the present invention may modulate an intensity of radiation of only a near-infrared light source exciting a parathyroid or turn on/off only the near-infrared light source and analyze (for example, a difference image analysis, a Fourier analysis, and a Modulation Transfer Function (MTF) analysis) an image in which a visible ray image and an autofluorescent image acquired in real time overlap to emphasize only an autofluorescence portion, in order to effectively separate the autofluorescent image having a small intensity of light from the visible ray image having a large intensity of light and emphasize the autofluorescent image Advantageous Effects According to the real-time parathyroid imaging device of the present invention, when Central Compartment Neck Dissection (CCND) for thyroidectomy is performed, a parathyroid is clearly marked by an autofluorescent image, thereby allowing a surgeon to more simply and safely perform the CCND while leaving the parathyroid.

BRIEF DESCRIPTION OF THE DRAWINGS

FIG. 14 is a graph of a spectrum of transmission of a notch filter (transmission of 350 to 400 nm: T>80, 400 to 1200 nm: T>90) allowing a wavelength, except for a wavelength of 785 nm, to pass through.

DETAILED DESCRIPTION

Best Mode

Hereinafter, an exemplary embodiment of a real-time parathyroid imaging device according to the present invention will be described in detail with reference to the accompanying drawings. The present invention is not limited to the exemplary embodiment disclosed below, but may be implemented into different various forms. The exemplary embodiment is provided only for making the disclosure of the present invention be complete and fully notifying those skilled in the art of the scope of the present invention.

In order to obtain an autofluorescent image of a parathyroid, which is desired to be displayed with a separate mark near a thyroid, by a real-time parathyroid imaging device according to the present invention, the real-time parathyroid imaging device basically needs to include a light source which is capable of exciting a parathyroid and a detector which is capable of detecting emission of autofluorescence. However, the parathyroid has a special absorption spectrum and emission spectrum, so that a light source and a detector appropriate to the special absorption spectrum and emission spectrum are required.

Figure 3:
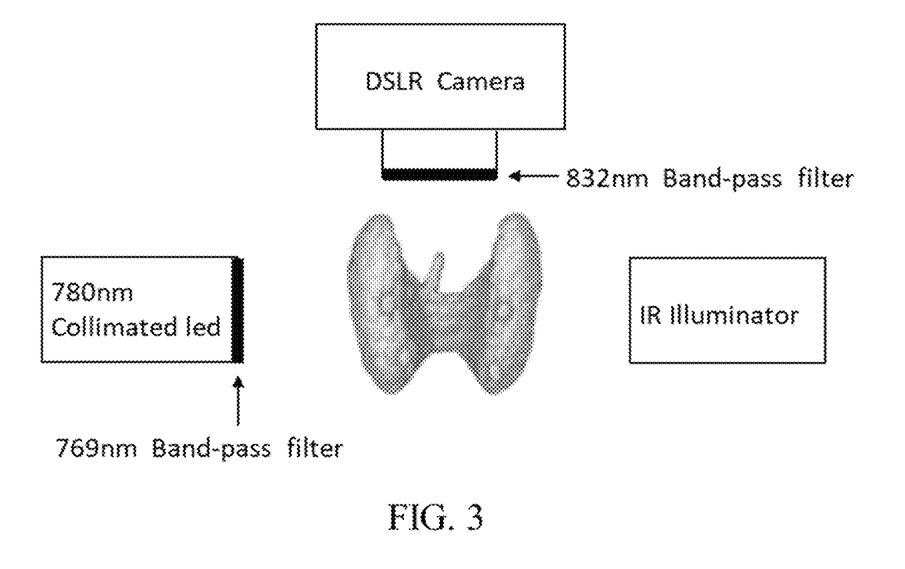
FIG. 3 is a diagram illustrating a real-time parathyroid imaging device according to an exemplary embodiment of the present invention.

In addition, an excitation spectrum and emission spectrum usually overlap, so that an excitation filter needs to be used in front of the light source and an emission filter needs to be used in front of the detector. Accordingly, as illustrated in FIG. 3, in the present invention, a collimated Light Emitting Diode (LED) light source of 200 mW having a peak wavelength of 780 nm as the light source is used as the light source, and a band-pass filter having a peak wavelength of 769 nm and a band width of 41 nm is disposed as the excitation filter in front of the light source. Further, as the detector, a Digital Single Lens Reflex (DSLR) camera or various cameras mounted with a Charged Coupled Device (CCD), a Complementary Metal Oxide Semiconductor (CMOS), a near-infrared sensor, or the like are used, and a band-pass filter having a peak wavelength of 832 nm and a band width of 37 nm is disposed in front of the detector. In addition, various collimated light sources, such as a laser diode, having a predetermined peak wavelength may be used as the light source.

Figure 4:
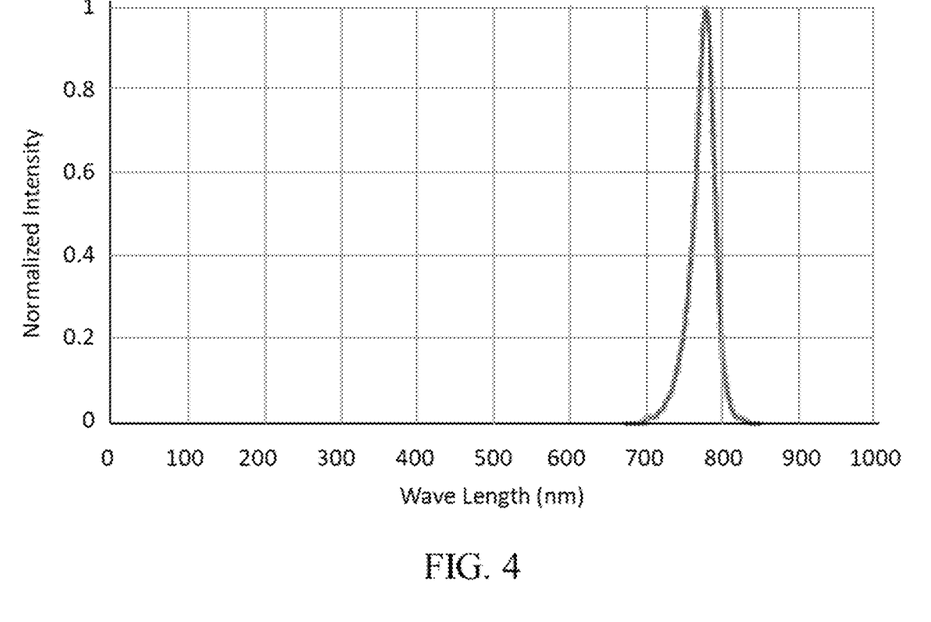
FIG. 4 is a graph of a spectrum of an LED light source of which a peak wavelength is 780 nm.
Figure 5:
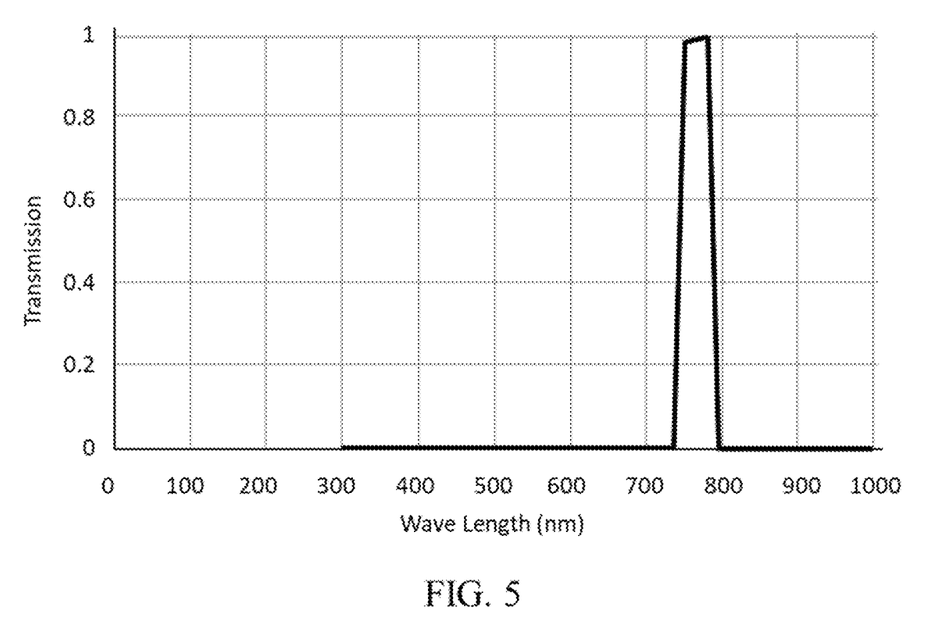
FIG. 5 is a graph of a spectrum of an excitation filter of which a peak wavelength is 769 nm and a band width is 41 nm.
Figure 6:
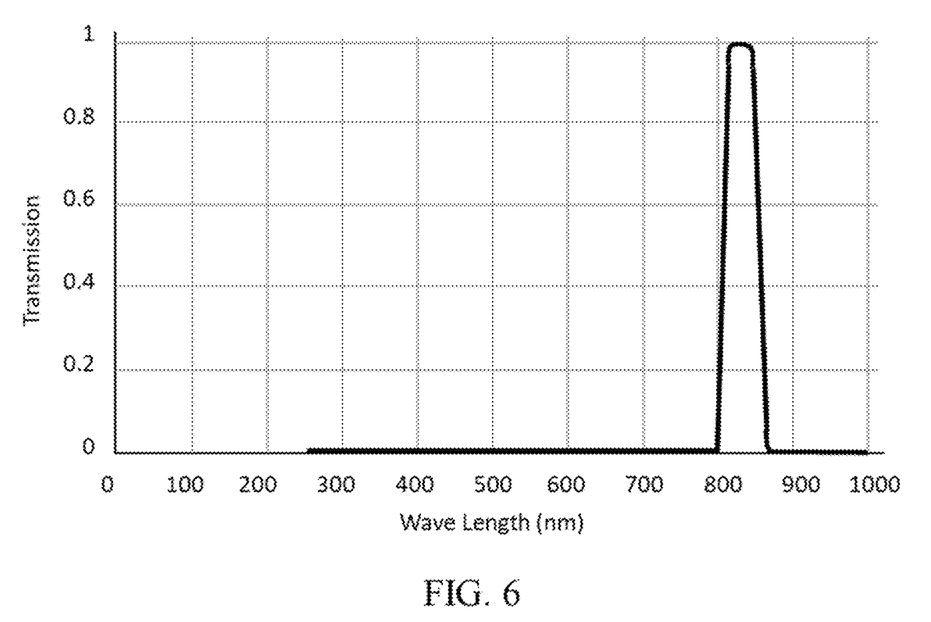
FIG. 6 is a graph of a spectrum of an emission filter of which a peak wavelength is 832 nm and a band width is 37 nm.
Figure 7:
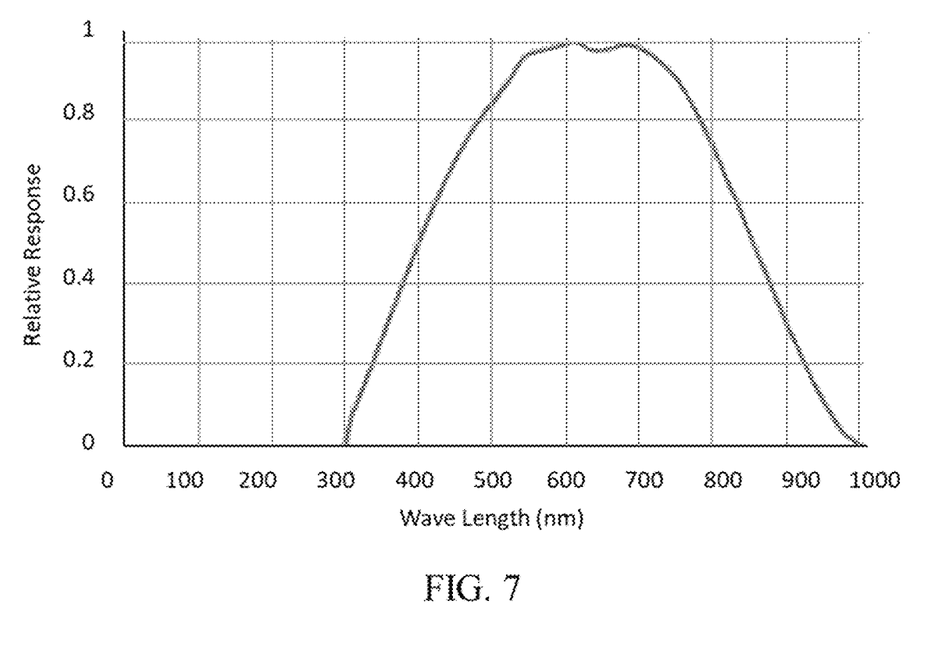
FIG. 7 is a graph illustrating sensitivity according to a wavelength of a Charge-Coupled Device (CCD) camera that is a detector in the real-time parathyroid imaging device according to the exemplary embodiment of the present invention.

FIG. 4 is a graph of a spectrum of an LED light source of which a peak wavelength is 780 nm, FIG. 5 is a graph of a spectrum of an excitation filter of which a peak wavelength is 769 nm and a band width is 41 nm, FIG. 6 is a graph of a spectrum of an emission filter of which a peak wavelength is 832 nm and a band width is 37 nm, and FIG. 7 is a graph illustrating sensitivity according to a wavelength of a CCD camera that is the detector in the real-time parathyroid imaging device according to the exemplary embodiment of the present invention. All of the graphs start from a wavelength of 200 nm, and normalized intensity of the LED light source spectrum is high at a peak wavelength, transmission of spectrums of the excitation filter and the emission filter at each peak wavelength is high, and sensitivity of the CCD camera is high at a specific wavelength, so that the imaging device according to the exemplary embodiment of the present invention displays an autofluorescent image of a parathyroid by appropriately utilizing the intensity, the transmission, and the sensitivity.

In order to obtain only the autofluorescent image of the parathyroid, all of the lighting devices (particularly, an astral lamp) in an operating room need to be turned off. Accordingly, in the present invention, in order to obtain the autofluorescent image of the parathyroid and surrounding tissue images together and check a location of the parathyroid, an Infrared Ray (IR) illuminator is used as illustrated in FIG. 3.

Figure 8:
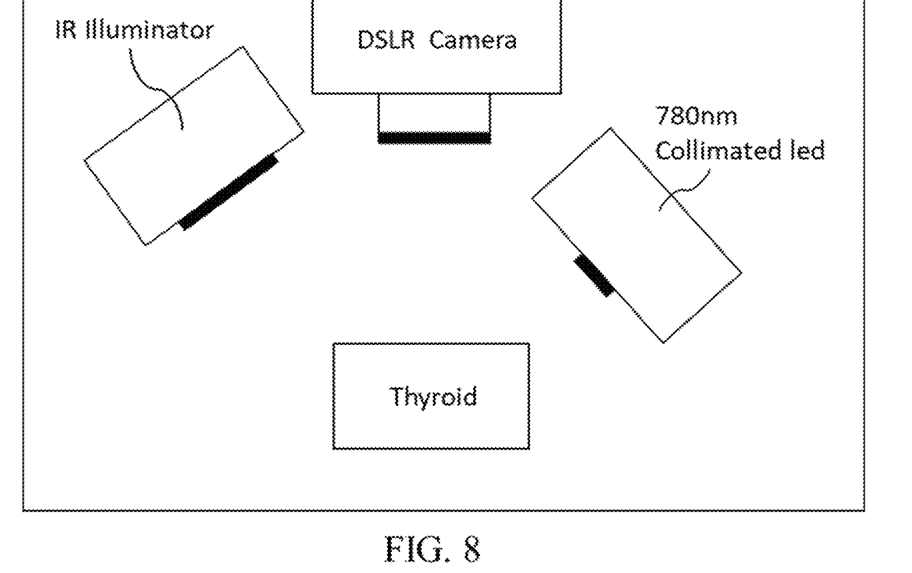
FIG. 8 is a picture illustrating an example, in which the real-time parathyroid imaging device according to the exemplary embodiment of the present invention is installed in an operating room.

FIG. 8 is a picture illustrating an example, in which the real-time parathyroid imaging device according to the exemplary embodiment of the present invention is installed in an operating room. As illustrated in FIG. 8, a collimated LED as the light source having a peak wavelength of 780 nm emits light toward a thyroid, and a DSLR camera as the detector disposed above the thyroid detects an autofluorescence spectrum emitted from a parathyroid by the light source, and photographs and detects an autofluorescent image of the parathyroid, and in this case, the IR illuminator disposed next to the DSLR camera emits infrared rays toward the thyroid to photograph and display the autofluorescent image of the parathyroid and surrounding tissue images together. A mark marking the emission spectrum of the parathyroid by the light source detected by the detector is the autofluorescent image.

Figure 9:
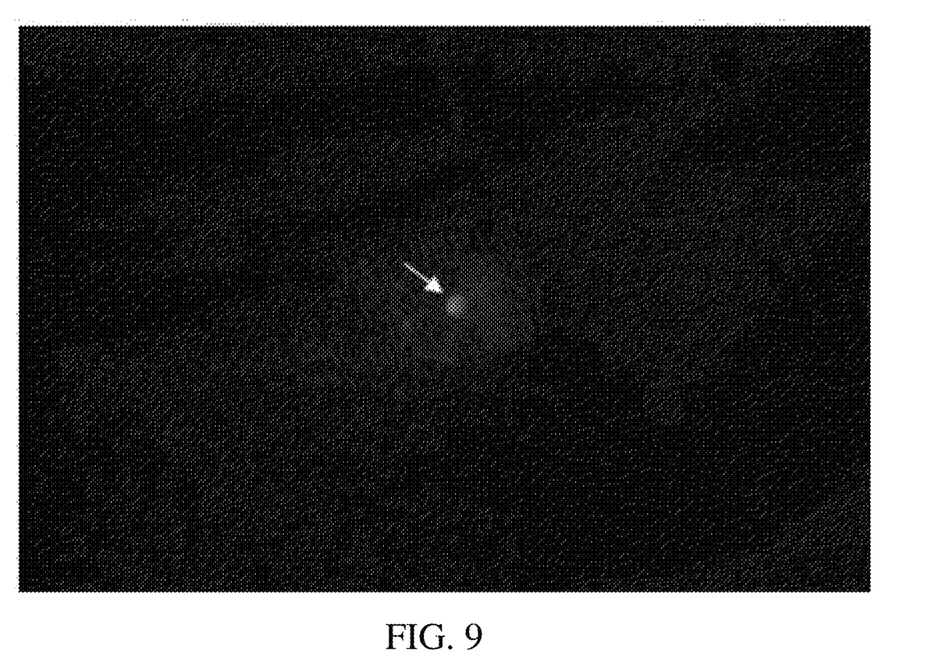
FIG. 9 is an autofluorescent image of a parathyroid by the real-time parathyroid imaging device according to the exemplary embodiment of the present invention.
Figure 10:
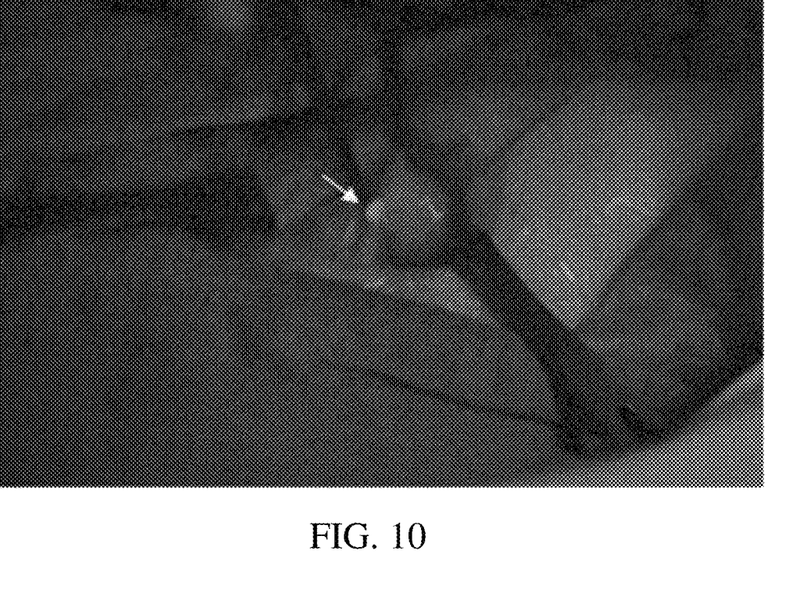
FIG. 10 is an image illustrating a comparison between a location of a parathyroid and surrounding tissues by an infrared ray illuminator.

FIG. 9 is a picture of only the autofluorescence of the parathyroid (arrow) obtained without using the IR illuminator of FIG. 3. The thyroid present around the parathyroid also faintly generates autofluorescence, but it can be seen that the autofluorescence of the parathyroid is prominent. FIG. 10 is a picture obtained by acquiring both an IR image and an autofluorescent image together by weakening an intensity of the IR illuminator and imaging the parathyroid and a background around the parathyroid at one time. In the image illustrated in FIG. 9, the parathyroid is confirmed, but a relationship with the surrounding structures is not recognized in an actual surgical field of view, so that the image is not a big help to a surgeon. Accordingly, like FIG. 10, an image, through which the parathyroid is confirmed in an actual surgical field of view and a surgeon can recognize a location of the parathyroid, is required.

Figure 11:
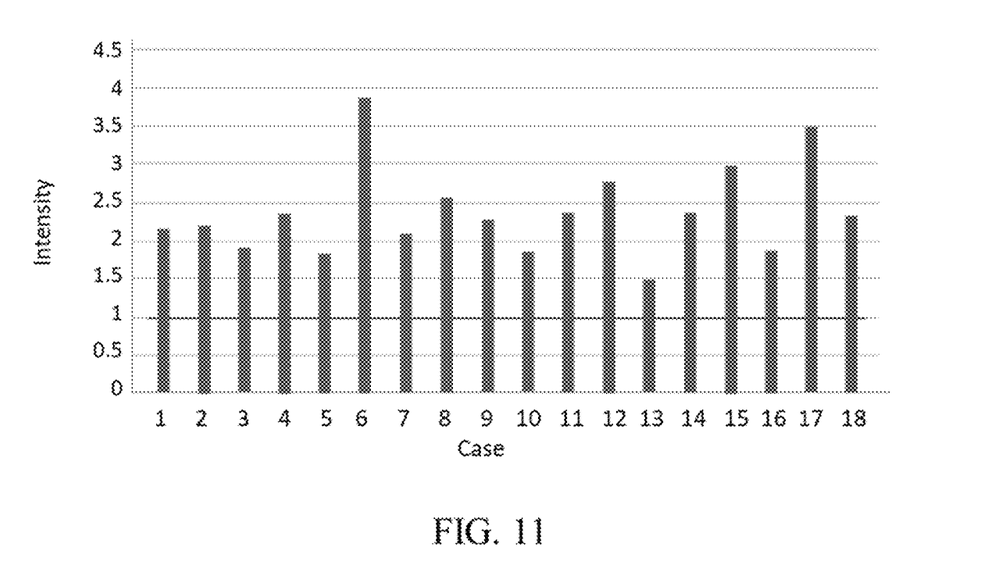
FIG. 11 is a graph of autofluorescence ratios of a parathyroid to a thyroid.

FIG. 11 represents a intensity ratio (P/T ratio) of the intensity in the autofluorescence of the parathyroid to the intensity in the autofluorescence of the thyroid. A total of 18 parathyroids were tested, and the intensity of all of the parathyroids are larger than that of the thyroid (P/T ratio>1). In the meantime, the sensitivity, which means the percentage of the case where the actual parathyroid is confirmed as the parathyroid by the autofluorescence method, is 100%, and specificity, which means the percentage of the case where the tissue that is not the actual parathyroid is not confirmed as the parathyroid by the autofluorescence method, is 80%.

Figure 12:
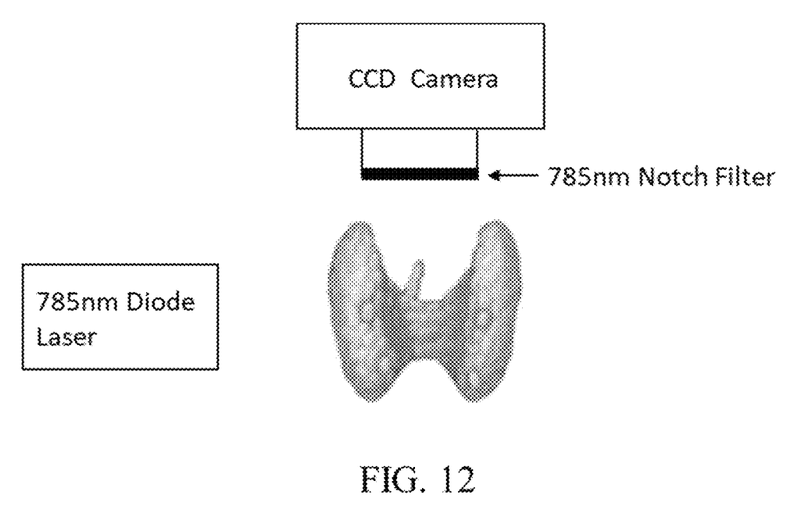
FIG. 12 is a diagram illustrating an example of a real-time parathyroid imaging device according to another exemplary embodiment of the present invention.
Figure 13:
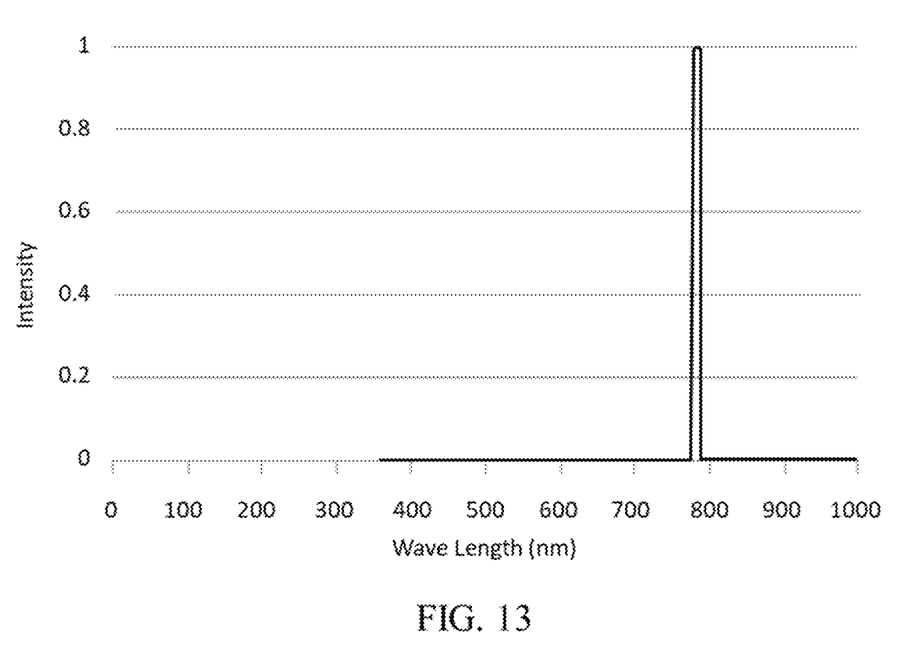
FIG. 13 is a graph of a spectrum of a laser diode light source of 785 nm having a narrowband of 3 nm.
Figure 14:
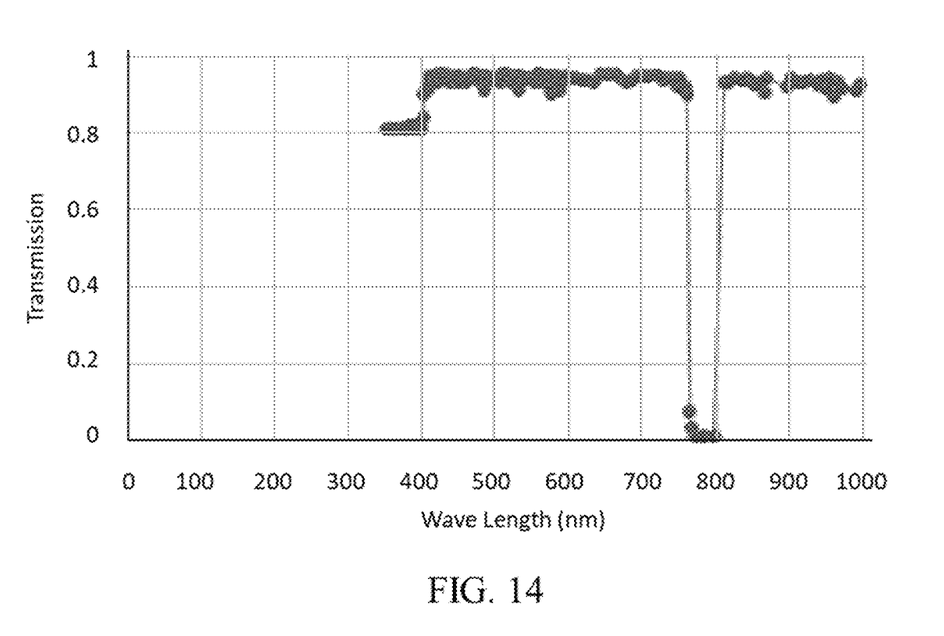
Figure 15:
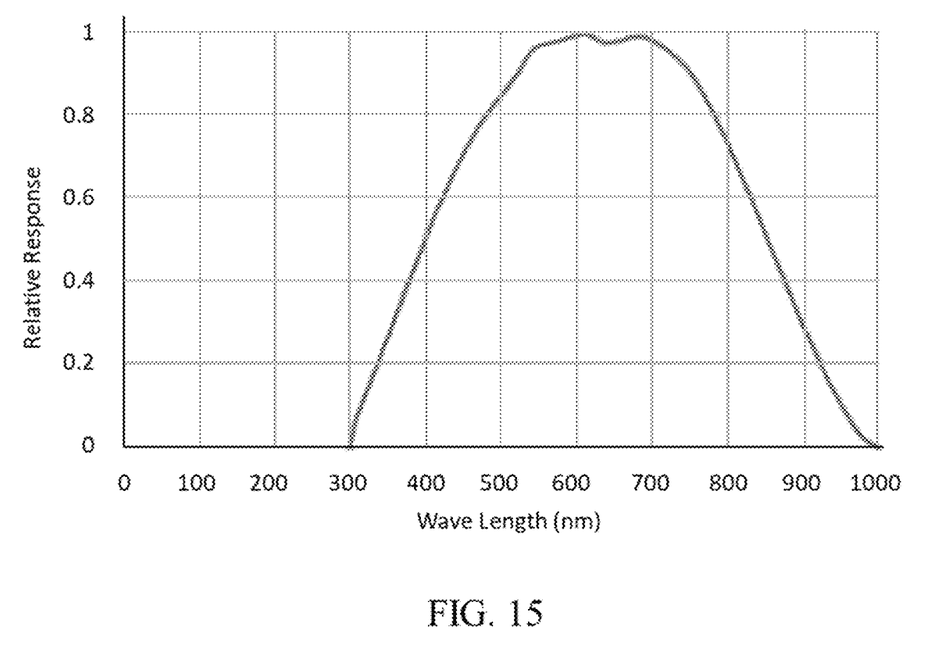
FIG. 15 is a graph illustrating sensitivity according to a wavelength of a CCD camera that is a detector in the real-time parathyroid imaging device according to another exemplary embodiment of the present invention.

In the exemplary embodiment of FIG. 3, in order to clearly obtain the autofluorescence of the parathyroid, the exposure of the camera needs to be considerably long. In a preparatory experiment, an exposure time is four seconds, so that for the real-time parathyroid imaging, in order to sufficiently supply power of a light source exciting autofluorescence and maximally transmit a spectrum of the emitted autofluorescence to a detector, there is suggested another exemplary embodiment of the present invention, in which an excitation light source is manufactured with a narrow-band light source using a laser diode of 785 nm and a notch filter (notch filter for removing a wavelength of 785 nm) is used so that all of the autofluorescence spectrums, except for only the narrow-band light source spectrum, reach the detector as illustrated in FIG. 12. FIG. 13 is a graph of a spectrum of a laser diode light source of 785 nm having a narrowband of 3 nm, FIG. 14 is a graph of a spectrum of transmission of a notch filter (transmission of 350 to 400 nm: T>80, 400 to 1200 nm: T>90) allowing a wavelength, except for a wavelength of 785 nm, to pass through, and FIG. 15 is a graph illustrating sensitivity according to a wavelength of a CCD camera that is a detector in the real-time parathyroid autofluorescence imaging device according to another exemplary embodiment of the present invention. An intensity of a spectrum of the laser diode light source at a peak wavelength is high and sensitivity of the CCD camera at a specific wavelength is high, so that the imaging device according to another exemplary embodiment of the present invention displays an autofluorescent image of a parathyroid by appropriately utilizing the intensity and the sensitivity.

In addition, as illustrated in FIG. 10, when an image is acquired only in the near-infrared region during the imaging of the parathyroid and the surrounding region of the parathyroid to an image, the acquired image is different from an image in a visible ray region recognized by a person, so that a surgeon is inconvenient to recognize a location of the parathyroid during surgery. Accordingly, instead of the image of FIG. 10, in order to provide an image in which a visible ray image and an autofluorescent image overlap like FIG. 16, visible rays are allowed to reach the CCD camera. However, an intensity of the visible rays reflected from the surrounding region of the parathyroid is considerably large compared to an intensity of the autofluorescence of the parathyroid, so that a manipulation of considerably limiting transmissivity of visible rays of the notch filter and increasing transmissivity of near-infrared rays is required as illustrated in FIG. 17. In order to provide the image in which a visible ray image and an autofluorescent image overlap, transmissivity of visible rays of the notch filter may be limited to be small, and transmissivity of near-infrared rays may be appropriately adjusted to be relatively large so that small amount of visible rays may reach the detector as well.

Figure 16:
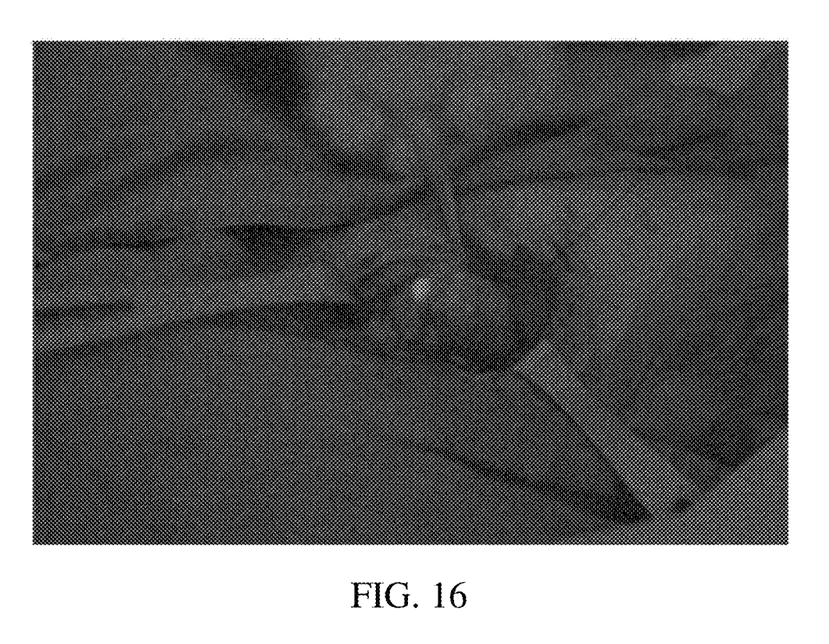
FIG. 16 is a picture obtained by overlapping a visible ray image and an autofluorescent image by the real-time parathyroid imaging device according to another exemplary embodiment of the present invention.
Figure 17:
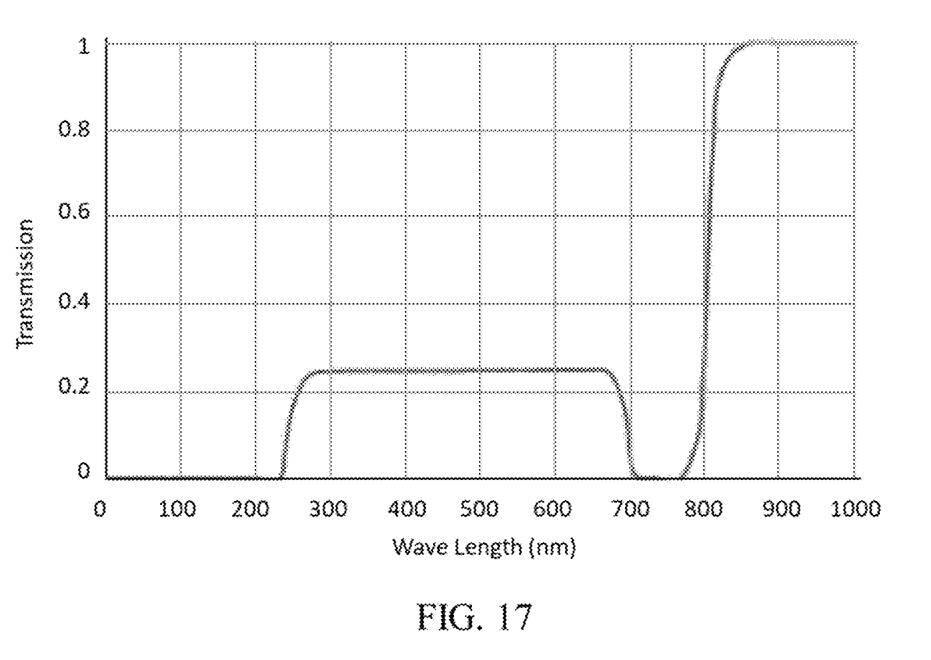
FIG. 17 is a graph illustrating a difference in transmission level according to a wavelength by a notch filter of the real-time parathyroid imaging device according to another exemplary embodiment of the present invention.

In the meantime, there is suggested a method of dividing the notch filter of FIG. 17 into two filters of a low-pass filter and a high-pass filter according to the need, and converting the autofluorescent image of the parathyroid of FIG. 9 or 10 into an autofluorescent image of the parathyroid of FIG. 16 by using an infrared ray illuminator if necessary. In order to provide the image in which a visible ray image and an autofluorescent image overlap, the notch filter may include the low-pass filter and the high-pass filter so that the visible rays reach the detector, and filtering of a pass or removal wavelength region of each of the low-pass filter and the high-pass filter may also be independently adjusted.

In addition, in order to effectively separate the autofluorescent image having a small intensity of light from a visible ray image having a large intensity of light and emphasize the autofluorescent image, a method of modulating the intensity of light of only the near-infrared light source exciting the parathyroid or turning on/off the near-infrared light source, and emphasizing only an autofluorescence portion through an analysis, for example, a difference image analysis, a Fourier analysis, and a Modulation Transfer Function (MTF) analysis, of a real-time obtained image illustrated in FIG. 16 may also be suggested.

In the foregoing, the real-time parathyroid imaging device according to the present invention has been described with reference to the drawings, but the present invention is not limited by the exemplary embodiment disclosed in the present specification and the drawing, and it is a matter of course that the present invention may be variously modified by those skilled in the art within the range of the technical spirit of the present invention.

What is claimed is:

1. A parathyroid imaging device for displaying a parathyroid, the parathyroid imaging device comprising:
   a light source configured to emit light to a thyroid and excite a parathyroid;
   an excitation filter disposed in front of the light source;
   an infrared ray illuminator which emits infrared rays toward a surgical field;
   a detector configured to detect an autofluorescent image with a background image, wherein the autofluorescent image is generated according to an autofluorescence spectrum emitted from the parathyroid; and
   an emission filter disposed in front of the detector,
   wherein the emission filter is for imaging simultaneously the parathyroid and the background around the parathyroid in the surgical field,
   wherein the emission filter includes a notch filter,
   wherein the notch filter is configured to pass through the near-infrared spectrum of the autofluorescence, the infrared spectrum of the illuminator and a visible spectrum, block the light source spectrum, and adjust transmissivity of visible rays and near-infrared rays.

2. The parathyroid imaging device of claim 1, wherein the light source is a Light Emitting Diode (LED) or a laser diode light source.

3. The parathyroid imaging device of claim 2, wherein the LED or laser diode light source is a collimated light source having a predetermined peak wavelength.

4. The parathyroid imaging device of claim 1, wherein the detector includes a Digital Single Lens Reflex (DSLR) camera, or a camera mounted with a Charged Coupled Device (CCD), a Complementary Metal Oxide Semiconductor (CMOS), or a near-infrared sensor.

5. The parathyroid imaging device of claim 1, wherein the excitation filter is a band-pass filter having a predetermined peak wavelength and band width.

6. The real-time parathyroid imaging device of claim 1, wherein the emission filter is a band-pass filter having a predetermined peak wavelength and band width.

7. The parathyroid imaging device of claim 1, wherein the excitation filter and the emission filter include band-pass filters having different peak wavelengths and bandwidths.

8. The real-time parathyroid imaging device of any one of claim 1, further comprising:
   an infrared ray illuminator which emits infrared rays toward the thyroid.

9. The parathyroid imaging device of claim 1, wherein the autofluorescent image of the emission spectrum of the parathyroid by the light source detected by the detector is displayed with a separate mark near a thyroid on a screen.

10. The real-time parathyroid imaging device of claim 9, wherein the light source is a laser diode light source, and the real-time parathyroid imaging device further includes a notch filter disposed in front of the detector so that all of the autofluorescence spectrums, except for a narrow-band light source spectrum by the laser diode light source, reaches the detector.

11. The parathyroid imaging device of claim 1,
    wherein the transmissivity of the near-infrared rays of the notch filter is adjusted to be relatively larger than transmissivity of visible rays of the notch filter so that the two images make the overlapped image with the best contrast.

12. The real-time parathyroid imaging device of claim 1, wherein in order to provide an image in which a visible ray image and an autofluorescent image overlap, the notch filter includes a low-pass filter and a high-pass filter each of which a filter region is independently adjusted so that the two images make an overlapped image with the best contrast.

13. The parathyroid imaging device of claim 1,
    wherein the parathyroid imaging device modulates an intensity of radiation of only a near-infrared light source exciting a parathyroid or turns on/off only the near-infrared light source and emphasizes an autofluorescent portion from an image in which a visible ray image and an autofluorescent image overlap, and
    wherein the parathyroid imaging device effectively separates the autofluorescent image having a small intensity of light from the visible ray image having a large intensity of light and emphasizes the autofluorescent image.

14. A parathyroid imaging device for displaying a parathyroid, the parathyroid imaging device comprising:
    a light source configured to emit light to a thyroid and excite a parathyroid;
    an excitation filter disposed in front of the light source;
    an infrared ray illuminator which emits infrared rays toward a surgical field;
    a detector configured to detect an autofluorescent image with a background image, wherein the autofluorescent image is generated according to an autofluorescence spectrum emitted from the parathyroid; and
    an emission filter disposed in front of the detector,
    wherein the emission filter is for imaging simultaneously the parathyroid and the background around the parathyroid in the surgical field,
    wherein the emission filter includes a band-pass,
    wherein the band-pass filter is configured to pass through a near-infrared spectrum of the autofluorescence and an infrared spectrum of the illuminator and block the light source spectrum.

* * * * *